(12) United States Patent
Rogers et al.

(10) Patent No.: US 6,355,828 B1
(45) Date of Patent: Mar. 12, 2002

(54) NITRILE PROCESS

(75) Inventors: Janet Marie Rogers; Robert Clifford Blackstone, both of Beaumont, TX (US); Jeffrey Jon Horsager, Woodbury, MN (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/710,996

(22) Filed: Nov. 10, 2000

(51) Int. Cl.$^7$ .............................................. C07C 255/03
(52) U.S. Cl. ...................................... 558/465; 558/466
(58) Field of Search .................................. 558/465, 466

(56) References Cited

U.S. PATENT DOCUMENTS

| | | | |
|---|---|---|---|
| 3,049,408 A | 8/1962 | Gause .......................... | 23/151 |
| 3,734,943 A | 5/1973 | Fitzgibbons et al. ..... | 260/465.3 |
| 3,936,360 A | 2/1976 | Wu .............................. | 203/75 |
| 4,238,295 A | 12/1980 | Odom .......................... | 203/83 |
| 4,269,667 A | 5/1981 | Landis ........................ | 203/76 |
| 4,981,670 A | 1/1991 | Dio et al. .................... | 423/376 |
| 6,084,121 A | 7/2000 | Rogers ........................ | 558/499 |

OTHER PUBLICATIONS

Masahiro Kurabayashi et al, Destabilization of Liquid Hydrogen and Stabilizer, Kogyo Kagaku Zasshi 71(7), 984–989 (1968?).

*Primary Examiner*—Floyd D. Higel
*Assistant Examiner*—Ebenezer Sackey

(57) ABSTRACT

A process for purifying a nitrile such as acrylonitrile is disclosed. The process comprises (1) contacting a product mixture, which comprises acrylonitrile and hydrogen cyanide, with an acid or a precursor of the acid to produce an acid-treated product; and (2) recovering the nitrile from the acid-treated product. The product mixture can be produced by contacting ammonia with a hydrocarbon such as an olefin under a condition effective to produce a nitrile and hydrogen cyanide.

20 Claims, No Drawings

NITRILE PROCESS

FIELD OF THE INVENTION

The present invention relates to a process for recovering or purifying a nitrile from a mixture comprising the nitrile and hydrogen cyanide and to a process for producing a nitrile, especially acrylonitrile, from a hydrocarbon and ammonia.

BACKGROUND OF THE INVENTION

A nitrile such as acrylonitrile or its derivative such as methacrylonitrile, is an important industrial chemical, especially in the plastics, surface coatings, and adhesive industries. For example, acrylonitrile can be used to produce acrylic fiber, as intermediate in the synthesis of antioxidants, pharmaceuticals, dyes, and surface-active agents. It can also be used as a modifier for natural polymers or as a pesticide fumigant agent for stored grain.

The production of acrylonitrile or its derivative by the catalytic ammoxidation of a hydrocarbon such as an olefin is well known and widely used. For example, the hydrocarbon used for producing acrylonitrile is propylene or propane. In this process, the hydrocarbon, ammonia and air are reacted over a catalyst at an elevated temperature, producing a vaporous mixture of acrylonitrile, acetonitrile, and hydrogen cyanide, along with water and other side-reaction products. The hot vapor is then cooled and quenched with sulfuric acid to remove unreacted ammonia. The vapor stream is then sent to a recovery system. It is first absorbed in water to create an aqueous stream containing the products of the reaction: acrylonitrile, acetonitrile, and hydrogen cyanide. The aqueous stream is then treated in a series of distillation columns to recover and purify these products. After the acetonitrile is removed for recovery, the hydrogen cyanide is stripped from the acrylonitrile stream, sent to a purification column, and chilled for storage.

Acetic acid is generally introduced during the separation of hydrogen cyanide from acrylonitrile. However, the use of acetic acid in the process has some disadvantages. Some of the acetic acid remains with the acrylonitrile stream, causing corrosion of metal equipment, and potentially remaining as an impurity in the acrylonitrile. In addition, it reacts with residual ammonia to form ammonium acetate, which is then carried by recycle streams back to the first part of the recovery and purification systems where it tends to decompose or release harmful ammonia to the process.

Stronger mineral acids such as phosphoric and sulfuric acids are also often used in processes for the direct production of hydrogen cyanide from methane or methanol as the carbon source. Since these processes produce few or little recoverable byproducts, the mineral acids do not affect the system adversely. However, mineral acids cannot be used in processes where acrylonitrile is the main product because they can react with acrylonitrile, especially under anhydrous conditions such as are found in acrylonitrile purification processes.

Therefore, there is an increasing need to develop a process for the purification of a nitrile such as, for example, acrylonitrile.

SUMMARY OF THE INVENTION

This invention comprises (1) contacting a mixture, which comprises a nitrile and hydrogen cyanide, with an acid having a pKa $\leq 4.4$ or a precursor of the acid to produce an acid-treated mixture; and (2) recovering the nitrile from the acid-treated mixture wherein the acid is not glycolic acid.

DETAILED DESCRIPTION OF THE INVENTION

According to the invention, the product mixture can be obtained from any source as long as the product mixture comprises a nitrile and hydrogen cyanide. Presently it is preferred that the product mixture be produced by a process which comprises contacting a hydrocarbon such as, for example, an olefin with ammonia and air to produce a product mixture comprising a nitrile and hydrogen cyanide.

The product mixture, which comprises a nitrile and hydrogen cyanide, is generally contacted with an acid, or a compound that produces the acid in-situ, to produce an acid-treated product. According to the invention, the product mixture can be contacted with the acid during the recovery or purification of the nitrile. The acid preferably has a pKa of $\leq 4.4$, more preferably $\leq 4.3$, and most preferably $\leq 4.2$. Generally, the lower end of the pKa is about 1.9. Examples of suitable acids include, but are not limited to, succinic acid, lactic acid, formic acid, glyceric acid, citric acid, fumaric acid, citraconic acid, maleic acid, sulfamic acid, esters of these acids, and combinations of two or more thereof.

The amount of acid or acid precursor used can be any quantity so long as the amount can substantially prevent the polymerization of the product mixture (or a component thereof) thereby facilitating the recovery or purification of the nitrile such as acrylonitrile. Generally, the molar ratio of acid to hydrogen cyanide present in the product mixture can be in the range of from about 0.001:1 to about 1000:1. Alternatively, the amount of acid or acid precursor is the amount that can lower the pH of the product mixture to about 4.2 or lower. The contacting can generally be carried out at a temperature in the range of from about 25° C. to about 130° C., preferably about 30° C. to about 100° C., under a pressure that can accommodate the temperature range, and for a time sufficient to separate, recover, or purify the nitrile, generally about 10 seconds to about 2 hours.

According to the invention, the term "nitrile" refers to a compound having the formula of RCN in which R is a hydrocarbyl radical having 1 to about 10 carbon atoms per radical. The presently preferred nitrites are acrylonitrile, methacrylonitrile, or combinations thereof. The hydrocarbon can be ethylene, propylene, isobutylene, butene, pentene, propane, or combinations of two or more thereof. The presently preferred hydrocarbon is propylene because acrylonitrile can be produced therefrom.

The contacting of hydrocarbon with ammonia and air is generally carried out in the gas phase in a suitable vessel such as, for example, a fluidized bed reactor having an air compressor and a quench column. A hydrocarbon such as, for example, propylene and ammonia can be vaporized and introduced into the vessel or reactor. The molar ratio of hydrocarbon to ammonia can be any ratio so long as a nitrile can be produced. Generally, the molar ratio can be in the range of from about 0.1:1 to about 10:1, preferably about 0.2:1 to about 5:1, and most preferably about 0.5:1 to about 2:1. The contacting can be carried out under any suitable condition such as a temperature in the range of from about 250 to about 600, preferably about 300 to about 550, and most preferably about 350 to about 500° C., under a pressure that can accommodate the temperature range, and for a time sufficient to produce a nitrile, generally about 10 seconds to about 2 hours.

The contacting of hydrocarbon with ammonia and air can also be carried out in the presence of an ammoxidation catalyst, as disclosed in U.S. Pat. Nos. 3,936,360 and 4,981,670, the disclosures of which are incorporated herein by reference. Because an amnuoxidation catalyst is well known to one skilled in the art, the disclosure of which is omitted herein for the interest of brevity. The contacting produces a product mixture comprising a nitrile and hydrogen cyanide, generally in gas or vapor phase.

Generally, a product mixture produced any source is cooled to a temperature in the range of from about 200 to about 270° C. to produce a cooled product mixture. The cooled product mixture is then quenched, with a quenching solution that comprises water and a recycled stream as defined in U.S. Pat. No. 3,936,360, to about 30 to about 90° C. to produce a quenched mixture. The quenched mixture is then contacted with sulfuic acid at about 70 to about 90° C. The amount of sulfuric acid can be any amount as long as it is sufficient to react any excess or ammonia to produce a quenched product.

The spent quenching solution can be generally further treated such that high-boiling materials, primarily catalyst fines, tars and other organic materials are concentrated, cooled, and routed to waste treatment along with the water generated by the contacting of olefm and ammonia.

Generally, the product mixture vapor can be routed to an absorber in which the organic materials are absorbed in chilled water. Nitrile and hydrogen cyanide, in the aqueous stream from the absorber containing the dissolved organic materials, are separated from the bulk of the water. Generally the separation can be carried out by azeotropic-extractive distillation, using water as the solvent. If the olefin is propylene, acetonitrile is generally also present in the product mixture and can be separated from acrylonitrile and hydrogen cyanide. The acrylonitrile and hydrogen cyanide are removed via the overhead stream and can be further purified. Acetonitrile and other organic materials are separated from the water in the bottom stream, which contains water and acetonitrile. The water can be recycled to serve as the solvent in both the absorber and the recovery of nitrile.

The product mixture can be further purified by any means known to one skilled in the art such as that disclosed in U.S. Pat. No. 3,936,360. Because the purification is well known, the description of which is omitted herein.

EXAMPLES

The following examples are intended to illustrate the invention but are not to be construed as to unduly limit its scope.

Each acid was tested by dissolving 1 gram of the acid into 125 ml. (~100 g.) of fresh plant stripper overheads. When fresh, this stream is almost colorless, but it normally develops color, nonvolatile material, and solids within 24 hours. Each sample was stored in a stoppered flask at room temperature and monitored periodically for color. After 1 month, the color development appeared to have slowed down, so the final color readings were taken. The samples were then discarded. A control sample without any acid and a second control sample using acetic acid were included.

This example illustrates that these acids are more effective stabilizing aids than acetic acid during the processing or storage of crude acrylonitrile streams, enabling the use of smaller quantities. The results are shown below.

| Acid | pKa | APHA Color[a] |
| --- | --- | --- |
| Adipic | 4.43 | 206 |
| Succinic | 4.16 | 38 |
| Lactic | 3.86 | 17 |
| Formic | 3.75 | 8 |
| Citric | 3.13 | 11 |
| Fumaric | 3.02 | 7 |
| Citraconic | 2.29 | 9 |
| Maleic | 1.94 | 12 |
| Sulfamic | 0.99 | 24 |
| Acetic | 4.75 | 60 |
| Glycolic | 3.83 | 16 |
| None (Control) | | Black and opaque with solids |

[a]APHA color is the American Public Health Association method of color determination based on a platinum-cobalt standard and was determined by spectrophotometry.

The results show that all acids tested and having a pKa of lower than 4.4 had a better results than acetic acid.

That which is claimed is:

1. A process comprising (1) contacting a mixture, which comprises a nitrile and hydrogen cyanide, with an acid or a precursor of said acid to produce an acid-treated mixture; and (2) recovering said nitrile from said acid-treated mixture wherein said acid has a pKa equal to or lower than 4.4 and said acid is not glycolic acid.

2. A process according to claim 1 wherein said nitrile is acrylonitrile and said acid has a pKa equal to or lower than 4.2.

3. A process according to claim 1 wherein said acid is succinic acid, lactic acid, formic acid, glyceric acid, citric acid, fumaric acid, citraconic acid, maleic acid, sulfamic acid, an ester thereof, or combinations of two or more thereof.

4. A process according to claim 2 wherein said acid is succinic acid, lactic acid, formic acid, glyceric acid, citric acid, fumaric acid, citraconic acid, maleic acid, sulfamic acid, an ester thereof, or combinations of two or more thereof.

5. A process according to claim 4 wherein the molar ratio of said acid to said hydrogen cyanide is in the range of from about 0.001:1 to about 1000:1.

6. A process according to claim 1 wherein said mixture is produced by reacting a hydrocarbon with ammonia to produce a mixture comprising acrylonitrile and hydrogen cyanide.

7. A process according to claim 5 wherein said mixture is produced by reacting an olefin with ammonia to produce a mixture comprising said acrylonitrile and hydrogen cyanide.

8. A process according to claim 7 wherein said mixture is produced by reacting propylene with ammonia to produce a mixture comprising acrylonitrile and hydrogen cyanide.

9. A process according to claim 6 wherein said mixture is produced by reacting propylene with ammonia to produce a mixture comprising acrylonitrile and hydrogen cyanide.

10. A process according to claim 9 wherein said acid is present in said mixture an amount sufficient to reduce the pH of the said mixture to below about 4.2.

11. A process according to claim 9 wherein said acid is formic acid.

12. A process comprising (1) reacting a hydrocarbon with ammonia to produce a mixture comprising a nitrile and hydrogen cyanide; (2) contacting said mixture with an acid having a pKa equal to or lower than 4.3 to produce an acid-treated mixture; and (3) recovering the nitrile from said acid-treated mixture.

13. A process according to claim 12 wherein said nitrile is acrylonitrile and said acid having a pKa equal to or lower than 4.2.

14. A process according to claim 12 wherein said acid is succinic acid, lactic acid, formic acid, glyceric acid, citric acid, fumaric acid, citraconic acid, maleic acid, sulfamic acid, an ester thereof, or combinations of two or more thereof.

15. A process according to claim 14 wherein the molar ratio of said acid to said hydrogen cyanide is in the range of from about 0.001:1 to about 1000:1 and said acid is formic acid.

16. A process according to claim 12 wherein said hydrocarbon is propylene and said nitrile is acrylonitrile.

17. A process comprising (1) reacting propylene with ammonia to produce a mixture comprising acrylonitrile and hydrogen cyanide; (2) contacting said mixture with an acid to produce an acid-treated mixture; and (3) recovering the acrylonitrile from said acid-treated mixture wherein said acid is succinic acid, lactic acid, formic acid, glyceric acid, citric acid, fumaric acid, citraconic acid, maleic acid, sulfamic acid, an ester thereof, or combinations of two or more thereof.

18. A process according to claim 17 wherein the molar ratio of said acid to said hydrogen cyanide is in the range of from about 0.001:1 to about 1000:1 and said acid is formic acid.

19. A process according to claim 18 wherein said acid is present in said mixture in an amount sufficient to reduce the pH of the said mixture to below about 4.2.

20. A process according to claim 19 wherein said process further comprises removing said arylonitrile and hydrogen cyanide before step (3).

* * * * *